(12) United States Patent
Narayan et al.

(10) Patent No.: US 6,489,503 B1
(45) Date of Patent: Dec. 3, 2002

(54) STORAGE STABLE METHYLENE BIS (PHENYLISOCYANATE) COMPOSITIONS

(75) Inventors: Thirumurti Narayan, Grosse Ile; Anthony Lunato; Jon S. Speier, both of Trenton; David D. Peters; Cynthia Loop, both of Wyandotte, all of MI (US); Filip Nevejans, St. Pauwels (BE)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 09/436,378

(22) Filed: Nov. 9, 1999

Related U.S. Application Data

(62) Division of application No. 09/157,876, filed on Sep. 21, 1998, now Pat. No. 6,120,699.

(51) Int. Cl.⁷ ............................................. C07C 267/00
(52) U.S. Cl. ....................... 560/26; 252/182.2; 548/951; 548/952; 560/27; 560/334; 560/336; 560/359
(58) Field of Search ............................ 560/26, 27, 334, 560/336, 359; 548/951, 952; 252/182.2

(56) References Cited

U.S. PATENT DOCUMENTS

| | | | |
|---|---|---|---|
| 4,031,026 A | * | 6/1977 | Ibbotson |
| 4,088,665 A | | 5/1978 | Findeisen et al. |
| 4,284,730 A | | 8/1981 | Narayan et al. |
| 4,743,626 A | | 5/1988 | Narayan |
| 4,743,627 A | | 5/1988 | Narayan et al. |
| 4,937,012 A | | 6/1990 | Kan et al. |
| 5,043,092 A | | 8/1991 | Pedain et al. |
| 5,489,620 A | * | 2/1996 | Bleys .......................... 521/170 |
| 5,663,272 A | * | 9/1997 | Slack et al. ................... 560/27 |

FOREIGN PATENT DOCUMENTS

EP    0 193 787 A    9/1986

* cited by examiner

Primary Examiner—John M. Cooney, Jr.
(74) Attorney, Agent, or Firm—Fernando A. Borrego

(57) ABSTRACT

The present invention provides a liquid methylene bis(phenylisocyanate) composition including a high concentration of methylene bis(phenylisocyanate) which has an improved storage stability. The invention further provides a method of making the liquid methylene bis(phenylisocyanate) compositions of the present invention.

22 Claims, No Drawings

STORAGE STABLE METHYLENE BIS (PHENYLISOCYANATE) COMPOSITIONS

This application is a division of application Ser. No. 09/157,876, filed Sep. 21, 1998, now U.S. Pat. No. 6,120,699.

BACKGROUND OF THE INVENTION

1. Technical Field

The invention relates to a liquid methylene bis (phenylisocyanate) composition having improved storage stability.

2. Description of Prior Art

Polyisocyanate compositions including a high concentration of methylene bis(phenylisocyanate) ("MDI"), particularly 4,4'-methylene bis(phenylisocyanate) ("4,4'-MDI"), while useful for various cellular and non-cellular polyurethane applications often pose a processing problem in that they are normally a solid at room temperature, i.e., about 25° C. The material, therefore, has to be melted and maintained in order to be useful as a liquid.

Unfortunately, methylene bis(phenylisocyanate) compositions having relatively high levels of 4,4'-MDI are also known to have a limited life due to the formation of diphenylmethane uretdione, otherwise referred to herein as uretdione. Uretdione tends to couple with the 4,4'-MDI molecules contained in methylene bis(phenylisocyanate) compositions, thereby forming a substantially insoluble precipitate over time. For example, 4,4'-MDI compositions maintained at about 43° C. for 14 days have exhibited uretdione concentrations above the generally acceptable saturation concentration of 0.5%. The formation of high concentrations of uretdione have heretofore rendered the methylene bis(phenylisocyanate) compositions substantially useless.

Interestingly, the uretdione reaction is both temperature and phase dependent. For example, as the temperature of a 4,4'-MDI composition is increased above about 43° C., the rate of uretdione formation increases. Further, the rate of uretdione formation is accelerated when the methylene bis(phenylisocyanate) is in the solid state as compared to a liquid composition at 43° C.; such formation being generally attributed to the alignment of the isocyanate groups in the crystal lattice structure.

In an effort to limit the formation of uretdione, methylene bis(phenylisocyanate) compositions, particularly 4,4'-MDI compositions, are often frozen and stored at temperatures below about 0° C. While this temporarily retards the formation of uretdione dimer, refrigerating the compositions for extended periods of time prior to use can be expensive and introduces logistic considerations which must be addressed.

It is, therefore, an object of the present invention to provide a liquid methylene bis(phenylisocyanate) composition which is storage stable at temperatures above about 30° C.

It is a further object of the invention to provide a liquid methylene bis(phenylisocyanate) composition which increases the saturation concentration of uretdione.

It is another object of the present invention to provide a methylene bis(phenylisocyanate) having a reduced freezing point.

It is still another object of the present invention to provide a liquid methylene bis(phenylisocyanate) composition which can be used in the preparation of all types of polyurethanes for which pure MDI is currently employed.

In view of the foregoing, the development of a liquid storage stable methylene bis(phenylisocyanate) composition including a high concentration of 4,4'-MDI that could be shipped in bulk, thereby reducing the high costs associated with shipping frozen drummed compositions would be highly desirable.

SUMMARY OF THE INVENTION

The foregoing objects, among others, are achieved by the methylene bis(phenylisocyanate) compositions of the present invention comprising a mixture of a) a methylene bis(phenylisocyanate) component including at least about 90.0 weight percent 4,4'-MDI; and b) an uretonimine. Under preferred embodiments, the uretonimine will be present in positive amounts of less than about 5.0 weight percent, based on the weight of the methylene bis(phenylisocyanate) composition. More preferably the uretonimine is present in amounts ranging from about 0.1 to less than about 5.0 parts per 100.0 parts of methylene bis(phenylisocyanate) composition, with amounts ranging from about 0.25 parts to about 2.5 parts being highly preferred. As will be described in greater detail below, a catalyst may be employed to cause the formation of uretonimine in situ. The amount of catalyst will generally range from about 0.0001 to about 5.0 parts, preferably about 0.0002 to about 2.5 parts, per 100.0 of methylene bis(phenylisocyanate).

The invention also provides a method of preparing storage stable liquid methylene bis(phenylisocyanate) compositions by admixing a methylene bis(phenylisocyanate) component including at least about 90.0 weight percent 4,4'MDI with an uretonimine to form a liquid methylene bis (phenylisocyanate) composition which is storage stable at temperatures as low as about 30° C.

Another method of the present invention relates to the in situ formation of uretonimine in liquid methylene bis (phenylisocyanate) composition including at least about 90.0 weight percent 4,4'-MDI.

DETAILED DESCRIPTION OF THE INVENTION

The methylene bis(phenylisocyanate) composition of the present invention comprises a) a methylene bis (phenylisocyanate) component including at least about 90.0 weight percent 4,4'-MDI; and b) an uretonimine.

The methylene bis(phenylisocyanate) component a) which includes at least about 90.0 weight percent 4,4'-MDI, more preferably will include at least about 95.0 weight percent 4,4'-MDI and under a highly preferred embodiment will include at least about 98.0 weight percent 4,4'-MDI. Generally, in addition to the 4,4'-MDI, the component a) may include 2,4'-MDI; 2,2'-MDI and other isomers, the 2,4'-MDI isomer being the predominant specie therein. The 2,4'-MDI isomer (and other MDI isomers) may make up the balance of the component a). Preferably, however, these isomers are limited to relatively low levels, i.e., about 2% or less by weight of component a).

The amount of methylene bis(phenylisocyanate) component a) in the composition of the present invention may be as low as about 80 weight percent, based on the total weight of the methylene bis(phenylisocyanate) composition. However, compositions of the present invention preferably comprise at least about 90.0 weight percent, more preferably at least about 95 weight percent, most preferably at least about 99 weight percent, of the methylene bis (phenylisocyanate) component.

In another aspect of the present invention, the source of uretonimine to the composition may contribute additional amounts of methylene bis(phenylisocyanate) isomers (predominantly 4,4'-MDI) to raise the level of methylene bis(phenylisocyanate) component in the composition, as described below. As such, the amount of methylene bis (phenylisocyanate) component a) in the composition of the present invention may be at least 97.5 weight percent, based on the total weight of the methylene bis(phenylisocyanate) composition, preferably at least about 98.75 weight percent, and still more preferably, at least about 99.75 weight percent. As described above, this component a) will predominantly comprise the 4,4'-MDI isomer, with the remainder of the methylene bis(phenylisocyanate) component (preferably 2% or less) comprising 2,4'-MDI and other isomers.

The methylene bis(phenylisocyanate) component a) can be produced by any of the commonly employed processes including the distillation of crude mixtures of isocyanate obtained by phosgenating a mixture of polyamines generally obtained by acid condensation of aniline and formaldehyde.

The uretonimine b) may be introduced into the methylene bis(phenylisocyanate) composition as part of an organic isocyanate blend or may be formed in situ in the methylene bis(phenylisocyanate) component to form the composition of the present invention. The uretonimine b) is generally formed by initially reacting, for example, 4,4'-MDI with a suitable catalyst such as a phospholene oxide with heating to give MDI carbodiimide. The MDI carbodiimide then reacts with excess 4,4'-MDI to give uretonimine groups as illustrated by the following reaction:

The uretonimine may be formed as described above from organic isocyanates including 2,4'-MDI and 2,2'-MDI isomers and mixtures thereof (particularly those comprising at least about 45 weight percent 4,4'-MDI), as well as aromatic, aliphatic and cycloaliphatic polyisocyanates and combinations thereof. Representative of these types are monoisocyanates including phenyl isocyanates, cyclohexyl isocyanate; the diisocyanates such as m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, hexahydrotoluene diisocyanate (and isomers), isophorone diisocyanate, hydrogenated methylene bis (phenylisocyanate), naphthalene-1,5 diisocyanate, 1-methoxyphenyl-2,4-diisocyanate, 4,4'-biphenylene diisocyanate, 3,3'-dimethoxy-4,4'-biphenyl diisocyanate, 3,3'-dimethyldiphenylmethane-4,4'-diisocyanate; the triisocyanate such as 4,4',4"-triphenylmethane triisocyanate and toluene 2,4,6-triisocyanate; and the tetraisocyanates such as 4,4'-dimethyldiphenylmethane-2,2',5,5'-tetraisocyanate and polymeric polyisocyanates such as polymethylene polyphenylene polyisocyanate, by way of non-limiting example. The reaction mechanism in each case is well known to those skilled in the art and are similar to the one exemplified above for production of the uretonimine from 4,4'-MDI.

The amount of uretonimine to be included in the methylene bis(phenylisocyanate) composition of the present invention will generally range from about 0.1 to about 5.0 parts per 100.0 parts of methylene bis(phenylisocyanate)

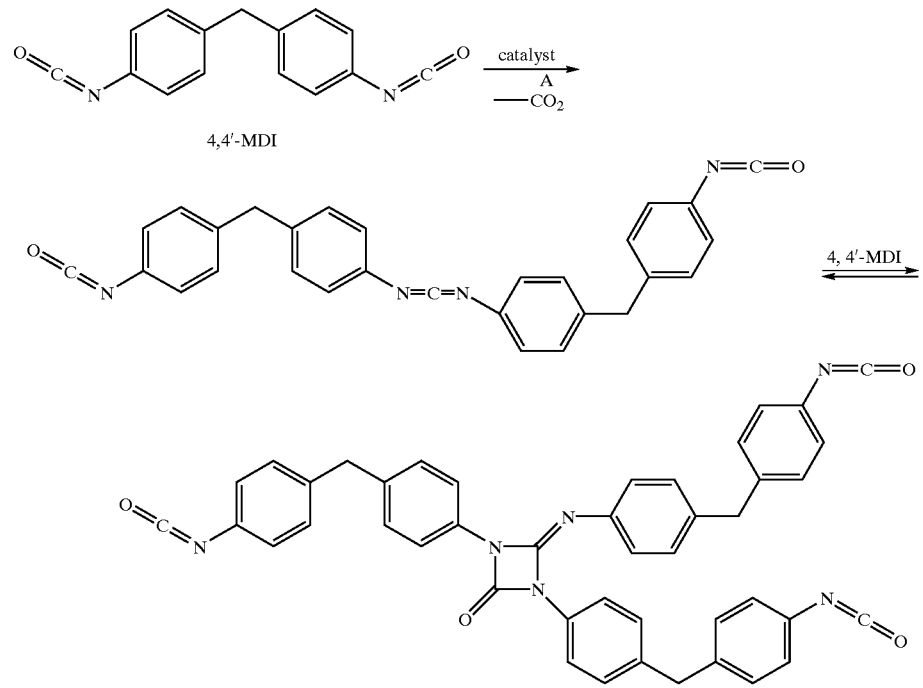

Thus, in the presence of excess 4,4'-MDI, the carbodiimide converts (but remains in equillibrium with the carbodiimide) to the uretonimine. This organic isocyanate blend, therefore, comprises uretonimine and methylene bis (phenylisocyanate), e.g., for example at ratios of 25:75, respectively. In the composition of the present invention, the amount of methylene bis(phenylisocyanate) takes into account amounts contributed thereto coming from the organic isocyanate blend.

composition, more preferably, from about 0.25 parts to about 2.5 parts, and most preferably from about 0.25 to about 1.25 parts per 100.0 parts of the composition.

In an alternative embodiment of the present invention, a desired amount of uretonimine is produced in situ in the methylene bis(phenylisocyanate) composition of the present invention, wherein a catalyst c) capable of reacting with 4,4'-MDI to give MDI carbodiimide, at least some of which is then converted to uretonimine in the presence of excess 4,4'-MDI, as described above. Thus, under certain embodiments, it may be desirable to add a catalyst c) into the methylene bis(phenylisocyanate) component a) to produce the storage stable liquid methylene bis(phenylisocyanate) compositions of the present invention.

Illustrative of such catalysts are:

(a) phospholene 1-oxides and 1-sulfides having the formulae:

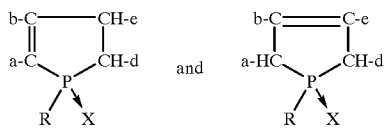

wherein a, b, c and d are each selected from the group consisting of hydrogen and hydrocarbyl from 1 to 12 carbon atoms inclusive, R is selected from the group consisting of lower alkyl and aryl and X is selected from the group consisting of oxygen and sulfur. The above phospholene compounds and methods for their preparation are described in U.S. Pat. Nos. 2,633,737, 2,663,738 and 2,853,473, which are hereby incorporated by reference. The 3-phospholenes can be isomerized readily to the corresponding 2-phospholenes by thermal treatment or by refluxing with an aqueous base as disclosed by Quin et al, Journal American Chemical Society, 33, 1024, 1968. Representative compounds within the above class are 1-phenyl-2-phospholene-1-oxide; 3-methyl-1-phenyl-2-phospholene-1-oxide; 1-phenyl-2-phospholene-1-sulfide; 1-ethyl-2-phospholene-1-oxide; 1-ethyl-3-methyl-2-phospholene-1-oxide; 1-ethyl-3-methyl-2-phospholene-1-sulfide; and the isomeric phospholenes corresponding to the above named compounds. Also, polymer bound phospholene oxide may be employed specifically those having recurring units, for example.

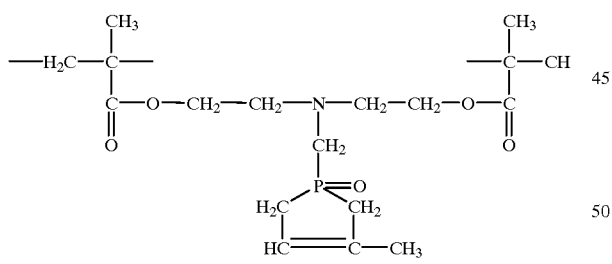

as disclosed in U.S. Pat. No. 4,105,643 and those of the following structure as disclosed in U.S. Pat. No. 4,105,642, both of which patents are expressly incorporated herein by reference.

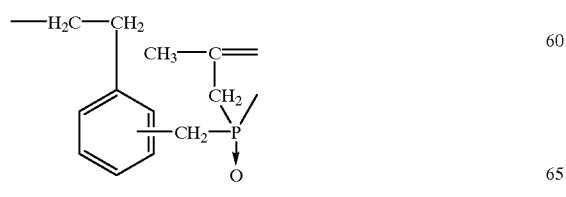

(b) diaza- and oxaza-phospholenes and -phosphorinanes

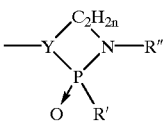

wherein $C_nH_{2n}$ represents alkylene from 1 to 12 carbon atoms, inclusive, at least one and not more than three adjacent carbon atoms and said alkylene radical forming a chain, one end of which is attached to Y, the other end of which is attached to N, thereby completing the heterocyclic ring; R' is selected from the group consisting of hydrocarbyl containing 1 to 12 carbon atoms, inclusive; and halo, nitro, alkoxy, alkyl, mercapto, and cyano substituted hydrocarbyl from 1 to 12 carbon atoms, inclusive; R" is hydrocarbyl containing from 1 to 12 carbon atoms, inclusive, and Y is selected from the group consisting of —O— and —NR"'— wherein R"' has the significance as defined above. The above compounds and methods for their preparation are described in U.S. Pat. No. 3,522,303. Representative examples of such compounds are: 2-ethyl-1,3-dimethyl-1,3,2-diazaphospholane-2-oxide; 2-chloromethyl-1,3-dimethyl-1,3,2-diazaphospholane-2-oxide; 2-trichloromethyl-1,3-dimethyl-1,3,2-diazaphospholane-2-oxide; 2-phenyl-1,3-dimethyl-1,3,2-diazaphospholane-2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1,3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3,2-diazaphospholane-2-oxide; 2-cyclohexyl-1,3-dimethyl-1,3,2-diaphospholane-2-oxide; 2-(2-ethoxyethyl)-1,3-dimethyl-1,3,2-diazaphospholane-2-oxide; and 2-naphthyl-1,3-dimethyl-1,3,2-diazaphospholane-2-oxide.

(c) Triaryl arsines wherein the aryl groups are free from substituents containing reactive hydrogen atoms, said arsine being represented by the formulae:

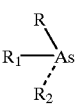

wherein each of R, $R_1$ and $R_2$ represents the same or different aryl moieties having from 6 to 12 carbon atoms, inclusive. Such compounds are described in U.S. Pat. No. 3,406,198. Representative examples are: triphenylarsine, tris(p-tolyl)arsine, tris(p-methoxyphenyl)arsine, tris(p-ethoxyphenyl)arsine, tris(p-chlorophenyl)arsine, tris(p-fluorophenyl) arsine, tris(2,5-xylyl)arsine, tris(p-cyanophenyl) arsine, tris(1-naphthyl)arsine, tris(p-methylmercaptophenyl)arsine, tris(p-biphenylyl) arsine, p-chlorophenyl bis(ptolyl)arsine and phenyl (p-chlorophenyl)(p-bromophenyl)arsine.

(d) Also included are compounds of the formula:

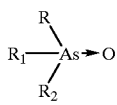

wherein each R, $R_1$ and $R_2$ represents the same or different alkyl or aryl groups having from 6 to 12 carbon atoms, inclusive. Representative examples of such are: triphenylarsine oxide, triethylarsine oxide, and polymer bound arsine oxide such as are described in U.S. Pat. No. 4,143,063:

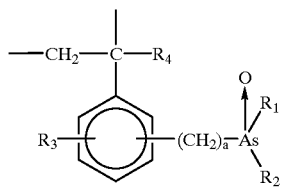

wherein $R_1$ and $R_2$ are hydrocarbyl from 1 to 12 carbon atoms inclusive, $R_3$ is hydrogen, chloro or methyl, $R_4$ is hydrogen or methyl, and n is 0 or 1.

(e) Metallic derivatives of acetylacetone such as the beryllium, aluminum, zirconium, chromium, and iron derivatives thereof as disclosed in U.S. Pat. No. 3,152,131.

(f) Phosphate esters of the formula:

$$(RO)_3PO$$

wherein R is hydrocarbyl from 1 to 12 carbon atoms, inclusive. Such esters and methods for their preparation are disclosed in U.S. Pat. No. 3,056,835. Representative examples are trimethylphosphate, triethylphosphate, ethyldipropylphosphate, triisopropylphosphate, triallylphosphate, triphenylphosphate and tricresylphosphate.

(g) Phosphine oxides of the formula:

$$R_3PO$$

wherein R is hydrocarbyl from 1 to 12 carbon atoms, inclusive. Representative examples are triethylphosphine oxide, tributylphosphine oxide, triphenylphosphine oxide and tris(chloromethyl)phosphine oxide.

(h) Metal complexes derived from a d-group transition element and π-bonding ligand selected from the group consisting of carbon monoxide, nitric oxide, hydrocarbylisocyanides, trihydrocarbylphosphine, trihydfrocarbylarsine, trihydrocarbylstilbine and dihydrocarbylsulfide wherein hydrocarbyl in each instance contains from 1 to 12 carbon atoms, inclusive, provided that at least one of the π-bonding ligands in the complex is carbon monoxide or hydrocarbylisocyanide. Such complexes and methods for the preparation are disclosed in U.S. Pat. No. 3,406,197. Representative examples of such complexes are iron pentacarbonyl, di-iron pentacarbonyl, tungsten hexacarbonyl, molybdenum hexacarbonyl, chromium hexacarbonyl, dimanganese decacarbonyl, nickel tetracarbonyl, ruthenium pentacarbonyl and the complex of iron tetracarbonyl: methylisocyanide.

The term "hydrocarbyl" from 1 to 12 carbon atoms inclusive employed herein means the monovalent radical obtained by removing one hydrogen atom from a parent hydrocarbon having the stated carbon atom content. Illustrative of such groups are alkyl such as methyl-, ethyl-, propyl-, butyl-, pentyl-, hexyl-, heptyl-, octyl-, nonyl-, decyl-, undecyl-, undodecyl-, including isomeric forms thereof; alkenyl such as allyl, butenyl, pentenyl, hexenyl, heptenyl, octenyl, nonenyl, decenyl, undecenyl and dodecenyl, including isomeric forms thereof; cycloalkyl such as cyclobutyl, cyclopentyl, cyclohexyl, cycloheptyl, cyclooctyl and the like; cycloalkenyls such as cyclopentenyl, cyclohexenyl, cycloheptenyl and the like; aralkyls such as benzyl, phenethyl, phenylpropyl, benzhydryl, naphthylmethyl and the like; and aryls such as phenyl, tolyl, xylyl, naphthyl, biphenylyl and the like.

The term "lower alkyl" as used herein means alkyl from 1 to 6 carbon atoms, inclusive, such a methyl, ethyl, propyl, butyl, pentyl, hexyl and isomeric forms thereof.

The preferred carbodiimide catalysts for use in preparing the compounds of the instant invention are the 1-phospholenes and 2-phospholenes, respectively. The preferred carbodiimide catalysts for use in preparing these compounds in accordance with the invention are the 1-aryl-3-lower alkyl-2-pholene 1-oxide and 1,3-di(lower alkyl)-2-phoslene 1-oxide, 1-phenyl-3-methyl-2-phospholene 1-oxide 1-ethyl-3-methyl-2-phospholene-1-oxide and the tris(chloromethyl)phosphine oxide. The most preferred phospholene oxide catalyst is 1H-phospholene, 2,5-dihydro-3-methyl-1-phenyl-1-oxide.

(i) Organotin compounds.

Organotin compounds may also be employed in the present invention. The Organotin compounds which may be employed in the present invention are both quadrivalent and divalent organotin compounds. The quadrivalent organotin compound may be described by the following formula:

wherein Z and Z' are individually alkyl, aryl, alicyclic, heterocyclic, oxyalkyl or acyloxy group having from 1 to 18 carbon atoms and may be the same or different, X is an alkyl, aryl, alicyclic, heterocyclic, oxyalkyl, acyloxy, thioalkyl or thioalkylene acyloxy group having 1 to 18 carbon atoms, Y is equal to X or oxy groups or a group represented by the following formula:

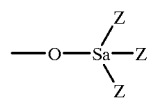

provided that when Y is this group, X is an alkyl or aryl group, m is equal to 1 except when Y is an oxy group then m is equal to 0 and a divalent organotin compound which may be described by the following formula:

$$Sn(OOCZ'')_2$$

wherein Z'' is alkyl, aryl, alicyclic, heterocyclic having from 1 to 18 carbon atoms. Those quadrivalent organotin compounds which may be employed as described in the formula above, are dibutyltin dilaurate, dibutyltin diacetate, dibutyltin di(2-ethylhexanoate), dioctyltin dilaurate, dibutyltin maleate, di(n-octyl)tin maleate, bis (dibutylacetoxytin) oxide, bis(dibutyllauroyloxytin) oxide, dibutyltin dibutoxide, dibutyltin dimethoxide, dibutyltin disalicilate, dibutyltin bis(isooctylmaleate), dibutyltin bis(isopropylmaleate), dibutyltin oxide, tributyltin acetate, tributyltin isopropyl succinate, tributyltin linoleate, tributyltin nicotinate, dimethyltin dilaurate, dimethyltin oxide, diotyltin oxide, bis(tributyltin) oxide, diphenyltin oxide, triphenyltin acetate, tri-n-propyltin acetate, tri-n-propyltin laurate and bis(tri-n-propyltin) oxide, dibutyltin dilaurylmercaptide, dibutyltin bis(isooctylmercaptoacetate) and bis(triphenyltin) oxide. Those preferred are dibutyltin diacetate, dibutyltin dilaurate, dibutyltin dilaurylmercaptide, dibutyltin bis(isooctylmercaptoacetate), dibutyltin oxide, bis(triphenyltin) oxide, bis(tri-n-butyltin) oxide. Those divalent organotin compounds which may be employed s catalysts as described in the formula above are: stannous oxalate, stannous oleate, stannous naphthenate, stannous acetate, stannous butyrate, stannous 2-ethylhexanoate, stannous laurate, stannous palmitate and stannous stearate. The preferred divalent tin compounds are stannous oxalate, stannous oleate and stannous 2-ethylhexanoate.

The catalyst c) which assists in forming uretonimine in the methylene bis(phenylisocyanate) compositions of the present invention as will be demonstrated in the following data, will generally be present in amounts ranging from 0.0001 parts to about 5.0 parts per 100 parts of methylene bis(phenylisocyanate) and preferably will range from about 0.0002 parts to about 2.5 parts, depending on the catalyst being employed.

For example, and without limitation, the phospholene oxides will generally range form about 0.0001 to about 0.1 parts per 100 parts methylene bis(phenylisocyanate) with a range of 0.0002 to 0.05 being preferred. The tricarbyl phosphates will, however, preferably range from about 0.1 to about 5.0 parts per 100 parts methylene bis (phenylisocyanate) with a range of 0.2 parts to about 2.5 parts being preferred.

To terminate the rate of uretonimine formation, a limited amount of acid can be added to the polyisocyanate composition to deactivate the catalyst. Useful catalyst deactivators include aliphatic and aromatic acid chlorides such as acetyl chloride, benzoyl m-chloride and benzenesulfonyl chloride, oxalyl chloride, adipyl chloride, sebacyl chloride and carbonyl chloride, by way of non-limiting example. Also inorganic acids such as perchloric acid and strong organic acids such as trifluoromethanesulfonic acid and trifluoroacetic acid may be employed.

Chloroformates may also be employed such as methyl chloroformate, ethyl chloroformate, isopropyl chloroformate, n-butyl chloroformate, isopropyl chloroformate, n-butyl chloroformate, sec-butyl chloroformate and diethylene glycol bis chloroformate.

A method for preparing of uretonimine modified methylene bis(phenylisocyanate) for blended compositions will now be described using two different catalysts.

Uretonimine Modified Isocyanate A

One thousand parts of a mixture of 98% 4,4- and 2.0% 2,4- isomers of methylene bis(phenylisocyanate) and 10 parts of triethyl phosphate are heated rapidly to 220° C. and maintained at that temperature for 2.5 to 3 hrs. The reaction contents are then rapidly cooled to 25° C. The product thus made displays an NCO content of 29.3% by weight and a viscosity of 40 cps at 25° C. The same procedure may be repeated to make compositions using methylene bis(phenylisocyanate) compositions having up to 55% 2,4'-isomer.

Uretonimine Modified Isocyanate B

One thousand parts of a mixture of 98% 4,4'- and 2.0% 2,4'- isomers of methylene bis(phenylisocyanate) are admixed with 0.004 parts of 3-methyl-1-phenyl-2-phospholene-1-oxide and rapidly heated to 105° C. and maintained at that temperature for 3–4 hrs. The reaction contents are then cooled to 70° C. and 0.04 parts of trifluromethane sulfonic acid is added to deactivate the catalyst. When the product is cooled to 25° C., it displays an NCO content of 29.3% by weight and a viscosity of 40 cps at 25° C. The same procedure may be repeated to make compositions using methylene bis(phenylisocyanate) compositions having up to 55% 2,4'-MDI isomer.

In addition to the foregoing uretonimine modified isocyanate compositions, certain similar commercially available uretonimine products such as MONDUR® CD available from Bayer Corporation, ISONATE® 143L and 143LM available from Dow Chemical Company, RUBINATE® LF 168 available from ICI Limited and LUPRINATE® MM103, available from BASF Corporation can be employed.

Experimental Results

Experiments are conducted to monitor the formation of uretdione over time at various temperatures to determine rates of formation, product lifetimes and uretdione saturation concentrations of the methylene bis(phenylisocyanate) compositions of the present invention. As such, samples of essentially pure MDI, i.e., 98.0% 4,4'-MDI (the remainder being predominantly 2,4'-MDI isomers and other isomers), are admixed with various amounts of uretonimine optionally with a catalyst as described in greater detail below.

EXAMPLE 1

A blend of 90% by weight of essentially pure 4,4'-MDI and 10% by weight of uretonimine modified isocyanate A, amounting to a calculated content of 97.5% 4,4'-MDI and 2.5% uretonimine, is prepared by mixing at 45° C. The contents are then cooled to 30° C. and stored at that temperature. The product remains as a stable liquid without any precipitation occurring for over three months at 30° C., whereas essentially pure 4,4'-MDI frozen at 30° C. has a useful lifetime of only four days. The same procedure is repeated with uretonimine modified MDI of isocyanate B to produce similar results.

EXAMPLE 2

A blend of 95% by weight of essentially pure 4,4'-MDI and 5.0% of uretonimine modified isocyanate A, amounting to a calculated content of 98.75% 4,4'-MDI and 1.25% of uretonimine, is prepared by mixing at 45° C. The product is then cooled and stored at 30–35° C. The product remains as a stable liquid for three months without any precipitation. The same procedure is repeated with the uretonimine modified isocyanate B which leads to the same results.

EXAMPLE 3

A blend of 99.0% by weight of essentially 4,4'-MDI and 1.0% by weight of uretonimine modified isocyanate A, amounting to 99.75% essentially 4,4'-MDI and 0.25% uretonimine, is prepared by mixing at 45° C. The product is stored at 43–45° C. An essentially pure 4,4'-MDI sample having no uretonimine reaches the saturation uretdione content in 15 days and commences precipitation while no precipitation is observed in the uretonimine-containing sample for 44 days. The same procedure is repeated using the uretonimine modified isocyanate B giving similar results.

A method of preparing uretonimine modified methylene bis(phenylisocyanate) in situ will now be described using two different catalysts.

EXAMPLE 4

One thousand parts of a mixture of an essentially pure 4,4'-MDI composition (containing about 98% 4,4'-MDI and about 2.0% or less of 2,4'-MDI isomers) and 10 parts of triethyl phosphate are rapidly heated to 220° C. and maintained at that temperature for 1 to 1.5 hr. It is then rapidly cooled to 30° C. The NCO content of the product is 33.0% and the calculated uretonimine content is 2.5%. Examination of the infrared spectrum of the product indicates the presence of peaks attributable to uretonimine moiety. As with the foregoing examples, no significant precipitation of uretdione is noted when stored at 30° C. for at least about 40 days.

EXAMPLE 5

One thousand parts of an essentially pure 4,4'-MDI composition and 0.002 parts of phospholene oxide are maintained at 45–50° C. for 5 hours. Thereafter, 0,02 parts of trifluromethane sulfonic acid is added to deactivate the catalyst. The product is cooled and stored at 30° C. The NCO content is 33.0% by weight. Again, no significant precipitation of uretdione is expected to occur at 30° C. for at least about 40 days.

The resulting storage stable liquid polyisocyanate composition of the present invention which includes a relatively high concentration of methylene bis(phenylisocyanate) can be used for multiple applications including those for which 4,4'-MDI is currently used. As such, the methylene bis(phenylisocyanate) compositions can be used in preparation of both cellular and non-cellular polyurethanes including, by way of non-limiting example, flexible, semi-rigid and rigid forms as well as elastomers as illustrated in Table I below.

Properties of cast elastomers prepared from the prepolymers based on the isocyanate of the present invention are compared in the following table with those prepared from the prepolymer based on essentially pure methylene bis(phenylisocyanate).

TABLE I

| Properties | A sample of the Example 1 composition was reacted with ethylene oxide tipped polyoxypropylene polyol of 1250 molecular weight to prepare a prepolymer having a free NCO content of 8% by weight, This prepolymer was chain extended with 1,4-butanediol and cast to produce an elastomer exhibiting the following characteristics | Commercially available essentially pure 4,4'-MDI product was reacted with ethylene oxide tipped polyoxypropylene polyol of 1250 molecular weight to prepare a prepolymer having an NCO content of 8% by weight. This prepolymer was chain extended with 1,4-butanediol and cast to produce an elastomer exhibiting the following characteristics |
| --- | --- | --- |
| Shore A hardness | 79 | 77 |
| 100% Modulus, psi | 790 | 820 |
| Tensile strength, psi | 2200 | 1400 |
| elongation, % | 450 | 210 |
| Tear (die C.), pli | 420 | 290 |
| Tabor Loss, mg | 113 | 150 |
| Compression set, % | 20 | 47 |
| Rebound, % | 48 | 29 |

Comparison of the properties in the above table indicates that the elastomers prepared from the isocyanate of the present invention displayed properties that are similar or better than those based on essentially pure 4,4'-methylene bis(phenylisocyanate) containing no uretonimine.

While it will be apparent that the preferred embodiments of the invention disclosed are well calculated to fulfill the objects stated, it will be appreciated that the invention is susceptible to modification, variation and change without departing from the spirit thereof.

What is claimed is:

1. A methylene bis(phenylisocyanate) composition having enhanced stability compared to pure methylene bis (phenylisocyanate) comprising, based on the total weight of the composition:
   a) at least about 90.0 weight percent of a methylene bis(phenylisocyanate) component including at least about 90.0 weight percent 4,4'-MDI; and
   b) a positive amount of 1.25 weight percent or less, of an uretonimine; wherein said methylene bis (phenylisocyanate) composition is storage stable as a liquid at a temperature of at least 30° C.

2. The methylene bis(phenylisocyanate) composition of claim 1, wherein said uretonimine is produced using a catalyst capable of converting an organic isocyanate into carbodiimide which in turn is converted into uretonimine in the presence of excess 4,4'-MDI.

3. The methylene bis(phenylisocyanate) composition of claim 2 wherein said catalyst is used in amounts of between about 0.0001 parts to about 5.0 parts per 100.0 parts methylene bis(phenylisocyanate).

4. The methylene bis(phenylisocyanate) composition of claim 2 wherein said catalyst is present in amounts of between about 0.0002 parts to about 2.5 parts per 100.0 parts methylene bis(phenylisocyanate).

5. The methylene bis(phenylisocyanate) composition of claim 2, wherein said organic isocyanate is selected from the group consisting of phenyl isocyanates, cyclohexyl isocyanate, methylene bis(phenylisocyanate) and toluene diisocyanate.

6. The methylene bis(phenylisocyanate) composition of claim 5, wherein said organic isocyanate comprises at least 45 weight percent 4,4'-MDI, the remainder comprising 2,4'-MDI and other MDI isomers.

7. The methylene bis(phenylisocyanate) composition of claim 1, wherein said uretonimine is produced in situ using a catalyst capable of converting a portion of said methylene bis(phenylisocyanate) component into carbodiimide which in turn is converted into uretonimine in the presence of excess 4,4'-MDI.

8. The methylene bis(phenylisocyanate) composition of claim 1 wherein said uretonimine is present in amounts of at least 0.1 parts per 100.0 parts methylene bis (phenylisocyanate) composition.

9. The methylene bis(phenylisocyanate) composition of claim 1 wherein said uretonimine is present in amounts of between about 0.25 weight percent to about 2.5 weight percent per 100.0 parts methylene bis(phenylisocyanate) composition.

10. The methylene bis(phenylisocyanate) composition of claim 2 wherein said catalyst is selected from the group consisting essentially of phospholene oxides, phosphates and mixtures thereof.

11. A methylene bis(phenylisocyanate) composition having enhanced stability compared to pure methylene bis (phenylisocyanate) comprising:
   a) a methylene bis(phenylisocyanate) component including at least about 90.0 weight percent 4,4'-MDI; and
   b) a positive amount of 1.25 weight percent or less, based on the weight of the composition, of an uretonimine
wherein said methylene bis(phenylisocyanate) composition is storage stable as a liquid.

12. The methylene bis(phenylisocyanate) composition of claim 11 wherein said methylene bis(phenylisocyanate) component is present in amounts of at least about 97.5 weight percent and said uretonimine is present in amounts of from about 0.25 to about 2.5 weight percent, based on the weight of the methylene bis(phenylisocyanate) composition.

13. The methylene bis(phenylisocyanate) composition of claim 11, wherein said uretonimine is produced using a catalyst capable of converting an organic isocyanate into carbodiimide which in turn is converted into uretonimine in the presence of excess 4,4'-MDI.

14. The methylene bis(phenylisocyanate) composition of claim 13 wherein said catalyst is used in amounts of between about 0.0002 parts to about 2.5 parts per 100.0 parts methylene bis(phenylisocyanate).

15. The methylene bis(phenylisocyanate) composition of claim 13, wherein said organic isocyanate is selected from the group consisting of phenyl isocyanates, cyclohexyl isocyanate, methylene bis(phenylisocyanate) and toluene diisocyanate.

16. The methylene bis(phenylisocyanate) composition of claim 15, wherein said organic isocyanate comprises at least 45 weight percent 4,4'-MDI, the remainder comprising 2,4'-MDI and other MDI isomers.

17. The methylene bis(phenylisocyanate) composition of claim 11 wherein said uretonimine is present in amounts of at least 0.1 parts per 100.0 parts methylene bis (phenylisocyanate) composition.

18. The methylene bis(phenylisocyanate) composition of claim 11 wherein said uretonimine is present in amounts of between about 0.25 weight percent to about 1.25 weight percent per 100.0 parts methylene bis(phenylisocyanate) composition.

19. The methylene bis(phenylisocyanate) composition of claim 13 wherein said catalyst is selected from the group consisting essentially of phospholene oxides, phosphates and mixtures thereof.

20. A polyisocyanate composition having enhanced stability compared to pure methylene bis(phenylisocyanate) comprising the reaction product of:
   a) a methylene bis(phenylisocyanate) component including at least about 90.0 weight percent 4,4'-MDI; and
   b) a catalyst capable of converting a portion of said 4,4'-MDT into carbodiimide, said carbodiimide being converted to uretonimine in the presence of excess 4,4'MDI, wherein said uretonimine is present in an amount of 1.25 weight percent or less, based on the weight of the composition,
wherein said composition is storage stable as a liquid.

21. A methylene bis(phenylisocyanate) composition having enhanced stability compared to pure methylene bis (phenylisocyanate) comprising, based on the total weight of the composition:
   a) at least about 90.0 weight percent of a methylene bis(phenylisocyanate) component including at least about 90.0 to about 98.0 weight percent 4,4'—MDI; the remainder comprising other MDI isomers or mixtures of said other MDI isomers; and
   b) a positive amount of less than about 5.0 weight percent of an uretonimine; wherein said methylene bis (phenylisocyanate) composition is storage stable as a liquid at a temperature of at least 30°C.

22. A methylene bis(phenylisocyanate) composition having enhanced stability compared to pure methylene bis (phenylisocyanate) comprising, based on the total weight of the composition:
   a) at least about 90.0 weight percent of a methylene bis(phenylisocyanate) component including a positive amount of about 2 weight percent or less of MDI isomers selected from the group consisting of 2,4'—MDI, 2,2'—MDI and mixtures thereof, the remainder comprising 4,4'—MDI; and
   b) a positive amount of less than about 5.0 weight percent of an uretonimine; wherein said methylene bis (phenylisocyanate) composition is storage stable as a liquid at a temperature of at least 30°C.

* * * * *

UNITED STATES PATENT AND TRADEMARK OFFICE
CERTIFICATE OF CORRECTION

PATENT NO. : 6,489,503 B1 Page 1 of 1
DATED : December 3, 2002
INVENTOR(S) : Thirumurti Narayan et al.

It is certified that error appears in the above-identified patent and that said Letters Patent is hereby corrected as shown below:

<u>Title page,</u>
Item [75], Inventors, please add -- Hans Volkmar Schwarz --

Signed and Sealed this

Thirteenth Day of January, 2004

JON W. DUDAS
*Acting Director of the United States Patent and Trademark Office*